United States Patent [19]

Tait

[11] 4,292,847
[45] Oct. 6, 1981

[54] TESTING THE MATERIAL OF A PRODUCT FOR DEFECTS THEREIN AND PROCESSING THE MATERIAL EMPLOYING SUCH A METHOD

[75] Inventor: William H. Tait, Hamilton, Canada
[73] Assignee: Dofasco Inc., Hamilton, Canada
[21] Appl. No.: 116,122
[22] Filed: Jan. 28, 1980
[51] Int. Cl.³ .............................................. G01N 29/04
[52] U.S. Cl. ......................................... 73/587; 73/658
[58] Field of Search .................. 73/587, 658, 659, 104, 73/801, 845

[56] References Cited

U.S. PATENT DOCUMENTS

| | | | |
|---|---|---|---|
| 3,793,627 | 2/1974 | Darrel et al. | 73/104 |
| 3,841,149 | 10/1974 | Edwin et al. | 73/104 |
| 4,087,801 | 5/1978 | Noh | 73/658 |

*Primary Examiner*—Anthony V. Ciarlante
*Attorney, Agent, or Firm*—Stanley J. Rogers

[57] ABSTRACT

A method of testing a product for the detection of the presence therein of a defect such as a void or an inclusion, comprises cutting the product and examining the resultant noise for the presence therein of an acoustic component representative of the presence of the inclusion. The method is applied to the processing of metal into slabs, bars, rods, wire strip etc., where the ends must be cropped to remove defective material, specifically to the continuous processing of strip metal where metal strips are joined continuously end-to-end, and where the ends of each strip as rolled may include undesired inclusions such as slag. A leading end piece is cropped by a shear, and the cropping of such pieces is continued until the testing method shows that the material at the place of the cut is free of the undesired inclusions.

8 Claims, 4 Drawing Figures

TESTING THE MATERIAL OF A PRODUCT FOR DEFECTS THEREIN AND PROCESSING THE MATERIAL EMPLOYING SUCH A METHOD

FIELD OF THE INVENTION

The present invention is concerned with improvements in or relating to methods of testing the material of a product for defects therein, for example, inclusions of unwanted foreign material, and to methods of processing such material employing such a method.

REVIEW OF THE PRIOR ART

It is now well known to evaluate and monitor the quality of certain products and processes by what is known as acoustic emission testing. In a typical system any acoustic emissions emanating from the test object are detected by a microphone that is sensitive over a wide range of frequencies and the resultant electric signal examined for components that will indicate the presence of defects such as cracks. These acoustic emissions may be generated spontaneously (e.g. during weld cooling, and with rotating parts and structures), or they may be the result of deliberate loading of the product under test (as with flex-and-pull testing).

A special problem encountered in the processing of steel results from defects which occur at the ends of a cast ingot or other piece of raw steel, particularly at the end that is last poured. It is difficult if not impossible to avoid the inclusion of some slag or shrinkage cavity which forms when the metal solidifies, at least at the said last-poured end, and these will remain in the material as it is rolled down to billets, slabs, bars, rods, wires, sheets, etc., in the form of an unwanted inhomogeneity or defect. Such defects are referred to as laminations or pipes, depending upon their shape and the type of rolled product and if too large, etc., can render the product unacceptable to the customer. The usual procedure has been therefore to crop the ends of the rolled material, the cropped ends being discarded. It is difficult to tell beforehand how much cropping is required, since for example, with a rolled sheet of about 0.3 cm to 0.6 cm., thickness this can vary between about 1 to about 20 meters. If the material is undercropped then faulty product is produced, while overcropping is of course wasteful.

The steel industry has been struggling with this problem for many years and most experimental work has been centered on ultrasonic testing, as being a relatively inexpensive continuous non-destructive method capable of detecting material flaws, but in practice it is almost impossible for the relatively delicate ultrasonic detectors to survive in the hostile operating environment of a pickle line and/or rolling mill.

DEFINITION OF THE INVENTION

It is therefore an object of the present invention to provide a new method of testing a product for the detection of an internal defect.

It is another object to provide a new method of processing a metal product having the possibility of a defect therein.

In accordance with the present invention there is provided a new method of testing a product for the presence of a defect in the material thereof, including the steps of:

(a) cutting a piece of the product;

(b) acoustically detecting the noise of the cutting and producing an electric signal representative thereof; and (c) examining the said electric signal to detect therein an acoustic component representative of a defect therein.

Also in accordance with the invention there is provided a method of processing a metal product having the possibility of an unwanted defect therein; including the steps of;

(a) cutting the product;

(b) acoustically detecting the noise of the cutting and producing an electric signal representative thereof;

(c) examining the said electric signal to detect therein a acoustic component representative of the defect to be detected;

(d) further processing the product in accordance with the detection or non-detection of the presence of the said defect.

DESCRIPTION OF THE DRAWINGS

Particular preferred embodiments of the invention will now be described, by way of example, with reference to the accompanying diagrammatic drawing, wherein.

DESCRIPTION OF THE PREFERRED EMBODIMENTS

Figure 1:
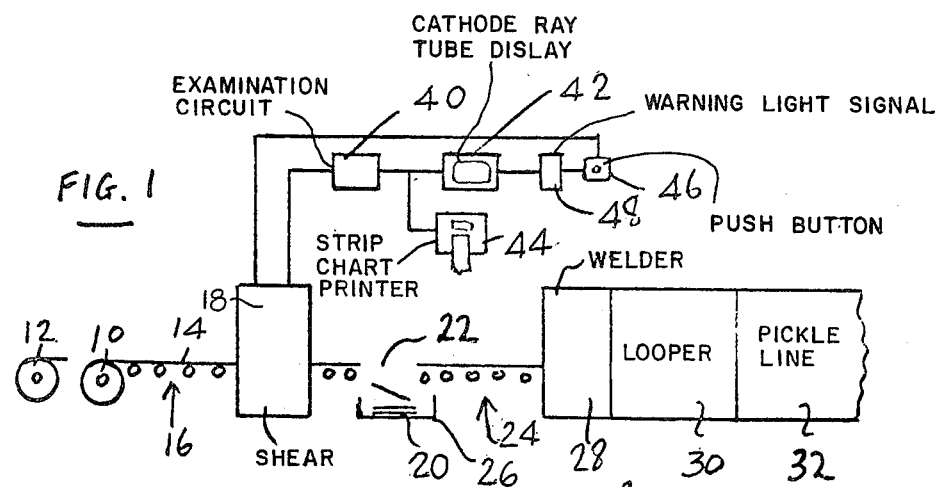
FIG. 1 is a schematic diagram of a steel strip pickle line employing the invention.

The invention is described in its application to the pickle line of a steel mill, since this is one of the first processes with which its application was considered, but the invention is applicable also to all processes in which cutting of the product is virtually an essential step so that there is an opportunity to investigate whether or not the product is defective, at least at the portion thereof at which the cut is made. A pickle line for steel strip is operated as a continuous process by welding the trailing edge of each strip to the leading edge of the succeeding strip. This leading edge must usually be cropped to remove any part thereof that contains lamination defects.

At the start of the line two coils 10 and 12 of the strip are provided, the coil 10 being mounted on a mandrel and unwinding, while the coil 12 is waiting until coil 10 is exhausted. The strip 14 passes along a conveyor 16 to a shear 18 in which the leading end is cropped, usually by about 1 meter at a time. The cropped pieces 20 pass from the shear and fall through a gap 22 in conveyor 24 into a waste bin 26. The cropping is continued as long as there is a detection of the presence of defects, and the resultant stripleading end is then passed to the welder 28 in which it is welded to the trailing end of the preceding strip which has been held waiting for this purpose by looper 30 ahead of the pickle line 32.

Figure 2:
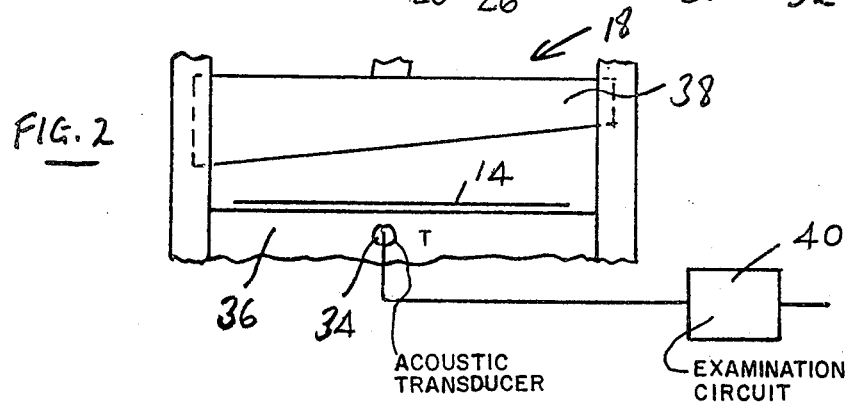
FIG. 2 illustrates the shear used to crop the steel strip and the placement of an acoustic detector in relation thereto.

In this embodiment the necessary detection is effected by means of an acoustic transducer 34 (FIG. 2), fixed to the stationary member 36 of the shear. As the shear blade 38 descends the transducer detects the noise made by the cutting action of the blade and feeds a resultant electric signal to a circuit 40 which will be described below. The output of circuit 40 may be fed to a cathode ray tube display unit 42 for direct display of the signal, using an appropriate time base and/or to a strip chart unit 44 which provides a "hard copy" of the transducer output.

Figure 3:
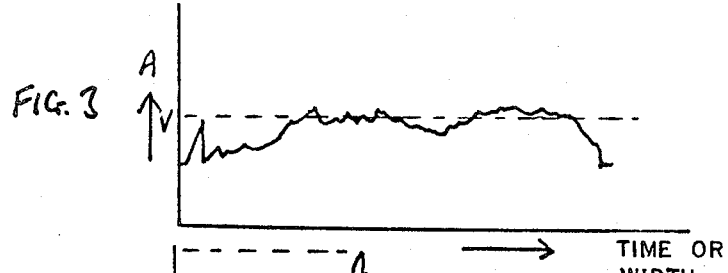
FIG. 3 shows a typical electric signal detected upon cutting at a defect-free part of the strip.
Figure 4:
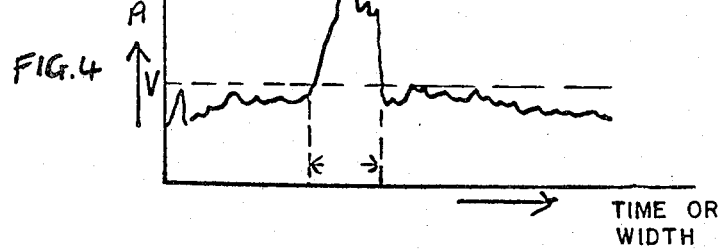
FIG. 4 is similar to FIG. 3 showing the signal detected upon cutting a defective part of the strip.

FIG. 3 shows a typical trace as produced by the unit 42 or 44 when the part of the strip through which the shear blade passes is free of defects, while FIG. 4 shows the trace that is obtained when a defect is present, consisting of a hidden lamination in about the middle of the sheet. FIGS. 3 and 4 are plots of the amplitude (A) of the signal from the transducer against time which, because of the progressive nature of the cut produced by the inclined knife blade, corresponds to width across the strip. The use of a progressive cut permits the ready display and examination of the electric signal because of the usable time base period between the start and end of the cut. It will be seen from FIG. 4 that the presence of a defect results in a sudden marked increase in the amplitude of the signal from the transducer, much above the predetermined average value V. Moreover, the location and the width W of the part of the signal above the value V gives an excellent indication of the location and the size of the defect. An operator viewing the unit 42 or 44 is therefore able to determine immediately whether or not an unwanted defect is present and, in the case that it is, operate a push button 46 to repeat the operation of the shear, this procedure being repeated until the signal shows no unwanted defect is present.

It is possible for the signal to be examined automatically by the circuit 40 and to operate the push button, or its equivalent, automatically upon detection of a defect of sufficient magnitude. The circuit may also be arranged to illuminate one or another of the lights of a light signal unit 48, a red light being lit when a defect is present. It is also possible for the circuit 40 to include more complex comparator means that will be able to distinguish between defects of a size and/or position that are inconsequential for the material that is being processed, so that their detection will not cause cropping of the material. The invention is as described above also applicable to the cropping of slabs and bars, the cropping again being continued with either manual or automatic surveillance until a defect-free end is indicated.

I claim:

1. A method of testing a product for the presence of a defect in the material thereof, including the steps of;
    (a) cutting a piece of the product;
    (b) automatically detecting the noise of the cutting and producing an electric signal representative thereof; and
    (c) examining the said electric signal to detect therein an acoustic component representative of a defect therein.

2. A method as claimed in claim 1, wherein the said electric signal is examined to detect the presence therein of an amplitude larger than a predetermined value, and including the step of continuing the cutting until such an amplitude is no longer present.

3. A method as claimed in claim 1 or 2, wherein the said cutting takes place with a progressive cut to provide a time base period during which the electric signal can be examined.

4. A method of processing a metal product having the possibility of an unwanted defect therein, including the steps of;
    (a) cutting the product;
    (b) acoustically detecting the noise of the cutting and producing an electric signal representative thereof;
    (c) examining the said electric signal to detect therein an acoustic component representative of the defect to be detected;
    (d) further processing the product in accordance with the detection or non-detection of the presence of the said defect.

5. A method as claimed in claim 4, including the step of repeating the cutting until the examination of the electric signal does not detect the presence of the unwanted defect.

6. A method as claimed in claim 5,
    wherein the said metal product is a continuous strip with which a plurality of elongated metal strips are to be joined end-to-end, and
    wherein the said further processing includes cutting at least one leading end piece from a succeeding strip before joining the succeeding strip to a preceding strip, and
    continuing the cutting of leading end-pieces from the said succeeding strip if the cutting step results in the detection of the presence of the said unwanted defect.

7. A method as claimed in any one of claims 4 to 6, wherein the processing is the rolling of metal and the ends of the rolled slab, bar, rod or sheet are cut until the cutting results in the non-detection of the said defect.

8. A method as claimed in any one of claims 4 to 6, wherein the cutting takes place with a progressive cut to provide a line base period during which the electric signal can be examined.

* * * * *